United States Patent
Nguyen et al.

(10) Patent No.: US 6,245,105 B1
(45) Date of Patent: Jun. 12, 2001

(54) METHOD OF TESTING BIOPROSTHETIC HEART VALVE LEAFLETS

(75) Inventors: Than Nguyen, Anaheim; Hung Ly Lam, Norco; Jianbo Zhou, Irvine; Carlos M. Romero, Orange; Ralph Kafesjian, Newport Beach; Xiaoming G. Guo, Dove Canyon; Van Le Huynh, Tustin, all of CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/207,783

(22) Filed: Dec. 9, 1998

Related U.S. Application Data

(63) Continuation of application No. 08/833,176, filed on Apr. 3, 1997, now Pat. No. 5,961,549.

(51) Int. Cl.[7] .................................................. A61F 2/24
(52) U.S. Cl. ...................................... 623/2.13; 73/865.3
(58) Field of Search ........................... 623/2, 912, 900, 623/2.12, 2.13; 73/865.3

(56) References Cited

U.S. PATENT DOCUMENTS

| | | |
|---|---|---|
| 4,388,735 | 6/1983 | Ionescu et al. . |
| 4,687,483 | 8/1987 | Fisher et al. . |
| 5,037,434 | 8/1991 | Lane . |
| 5,376,110 | 12/1994 | Tu et al. . |
| 5,549,666 | 8/1996 | Hata et al. . |
| 5,613,982 | 3/1997 | Goldstein . |
| 5,718,012 | 2/1998 | Cavallaro . |
| 5,899,937 | * 5/1999 | Goldstein et al. ................. 623/2 |
| 5,961,549 | * 10/1999 | Nguyen et al. .................... 623/2 |

FOREIGN PATENT DOCUMENTS

| | | |
|---|---|---|
| 0133420 | 2/1985 | (EP) . |

OTHER PUBLICATIONS

Sacks, "Biaxial Mechanical Behavior of Fixed Bovine Pericardium", Fifth World Biomaterials Congress, Toronto, Canada, May 29–Jun. 2, 1996.

Simionescu, et al., "Mapping of Glutaraldehyde–Treated Bovine Pericardium and Tissue Selection for Bioprosthetic Heart Valves", Journal of Biomedical Materials Research, vol. 27, 697–703, 1993.

Zioupos, et al., "Anisotropic Elasticity and Strength of Glutaraldehyde Fixed Bovine Pericadium for Use in Pericardial Bioprosthe tic Valves", Journal of Biomedical Materials Research, vol. 28, 49–57, 1994.

* cited by examiner

*Primary Examiner*—Bruce Snow
(74) *Attorney, Agent, or Firm*—Guy L. Cumberbatch; Debra D. Condino

(57) ABSTRACT

Heart valve leaflet selection methods and apparatuses which subject individual leaflets to loads and measure the resulting deflection to more reliably group leaflets of similar physical characteristics for later assembly in prosthetic heart valves. The deflection testing may be accomplished using a variety of test set ups which are designed to impart a load on the leaflet which simulates the actual loading within a heart valve. The results from a number of deflection tests are used to categorize individual leaflets, which data can be combined with other data regarding the characteristics of the leaflet to better select leaflets for assembly into a multi-leaflet heart valve. In one embodiment, the deflection test is combined with an intrinsic load test, and leaflets having similar deflection and intrinsic load values used in the same heart valve. One apparatus for testing the leaflets includes a frame for securing the arcuate cusp of the leaflet while the straight coapting edge remains free, to simulate the actual leaflet mounting configuration within the heart valve prosthesis. The frame may include a lower portion having a recess for the leaflet and plurality of receptor holes around the peripheral edge of the recess, and an upper portion having a plurality of needles which extend downward through the leaflet and into the receptor holes and secure the edges of the leaflet.

41 Claims, 9 Drawing Sheets

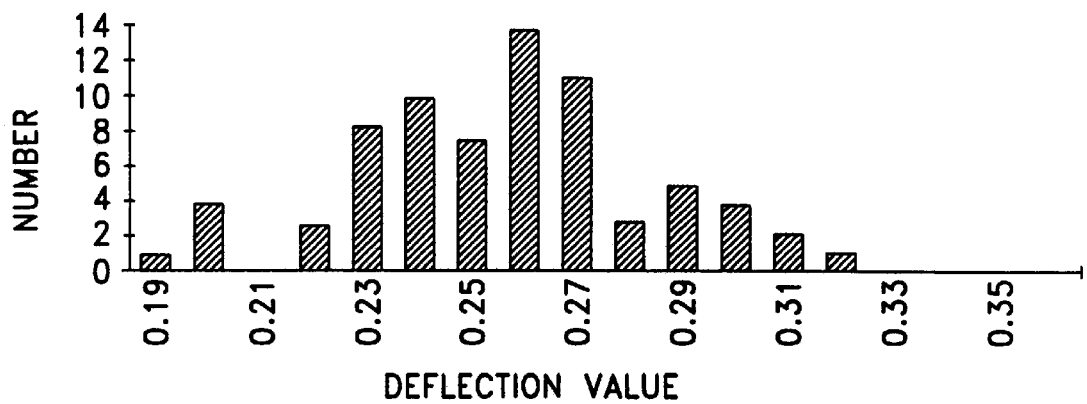
FIG.10A DROOP A CATEGORY
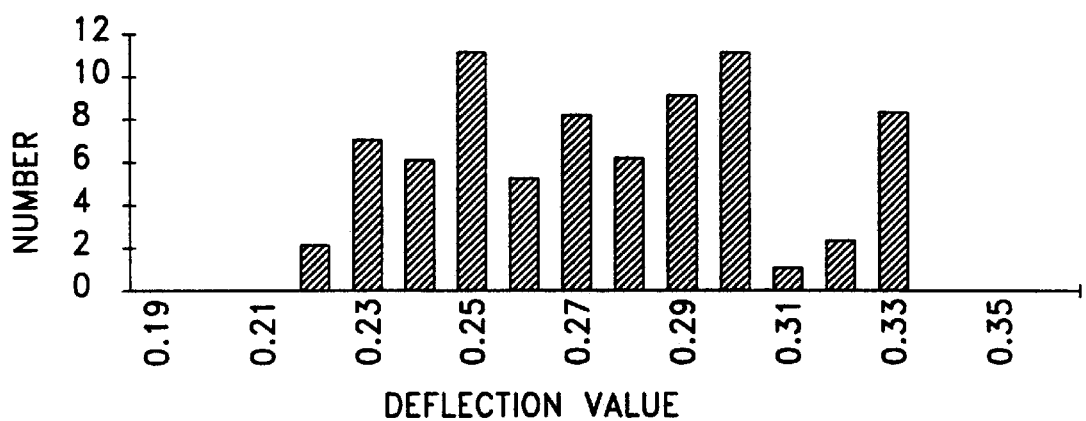
FIG.10B DROOP B CATEGORY
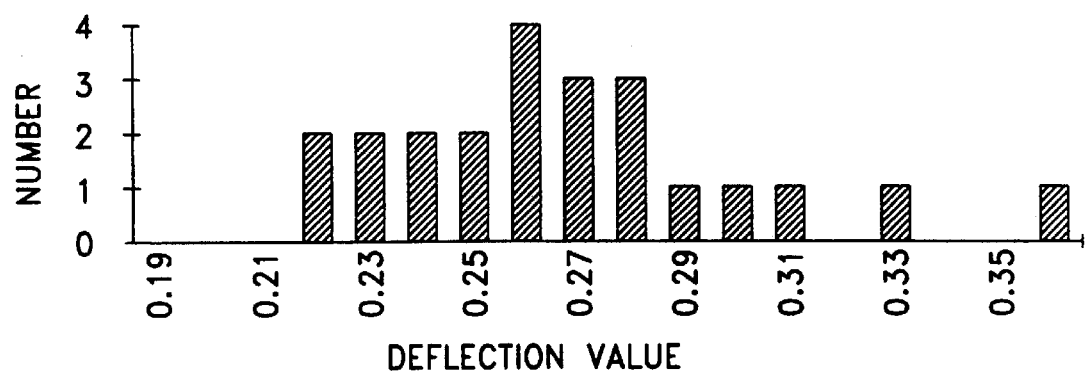
FIG.10C DROOP C CATEGORY

METHOD OF TESTING BIOPROSTHETIC HEART VALVE LEAFLETS

RELATED APPLICATIONS

The present application is a continuation of U.S. application Ser. No. 08/833,176, filed Apr. 3, 1997, now U.S. Pat. No. 5,961,549 and entitled "MULTI-LEAFLET BIOPROSTHETIC HEART VALVE".

FIELD OF THE INVENTION

The present invention relates to methods for selecting leaflets for use in a prosthetic heart valve, and, more particularly, to methods and apparatuses for selecting individual pericardial leaflets for a multi-leaflet heart valve prosthesis.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid, and pulmonary valves. Prosthetic heart valves can be used to replace any of these natural valves. The two primary types of prosthetic heart valves known in the art are mechanical valves and bio- prosthetic valves. Mechanical valves include rigid leaflets and a pivoting mechanism, and bio- prosthetic valves utilize flexible tissue leaflets, typically mounted to a manufactured support frame. The present invention provides methods for selecting leaflets in bio-prosthetic valves.

Bio-prosthetic valves may be formed from an intact, multi-leaflet porcine (pig) heart valve, or by shaping a plurality of individual leaflets out of bovine pericardial tissue and combining the leaflets to form the valve. The pericardium is a sac around the heart of vertebrate animals, and bovine (cow) pericardium is commonly used to make individual leaflets for prosthetic heart valves. The bovine pericardium is first harvested from the animal and then chemically fixed to crosslink collagen and elastin molecules in the tissue and increase the tissue durability, before being cut into leaflets. Various physical characteristics of the tissue may be examined before or after fixation.

One drawback faced by a patient having an implanted bio-prosthetic heart valve is the potential for calcification of the leaflets if the valve remains in place for an extended period of time (more than ten years). Calcification tends to make the leaflets less flexible. A significant amount of research has been accomplished in mitigating calcification of bovine pericardial leaflets to lengthen the useable life of the heart valve. Calcification may reduce the performance of the heart valve, and thus, the highest quality materials and design in the heart valve is required to forestall a failure of the valve from excessive calcium deposits.

Despite the drawbacks of artificial heart valve material, over twenty years of clinical experience surrounding implanted artificial heart valves has produced a proven track record of success. Research in extending the useful life of the bio-prosthetic valves continues, however. One aspect of designing heart valves which is very important in improving their performance is the selection of the pericardial tissue used in the leaflets. In all heart valves, the natural action of the flexible heart valve leaflets, which seal against each other, or co-apt, is desirable. The difficulty in simulating the leaflet movement of an actual heart valve (especially a mitral valve) in a prosthetic valve is that the leaflets used are "inanimate." There are no muscular attachments to the leaflets as in the natural valve, and the prosthetic leaflets must co-apt to function properly solely in response to the fluid pressures within the heart chambers. Indeed, natural coaptation of the leaflets in bio-prosthetic valves comprising a plurality of individual leaflets sewn together is particularly difficult, even when compared to inanimate but intact valves, such as harvested porcine valves.

Much of this research involves the mechanical properties of fresh or fixed bovine pericardium. A good discussion of the various physical properties of fixed bovine pericardium is given in Simonescu, et al, *Mapping of Glutaraldehyde-Treated Bovine Pericardium and Tissue Selection For Bioprosthetic Heart Valves,* Journal of Bio-Medical Materials Research, Vol. 27, 1993. Simionescu, et al, recognized the sometimes striking variations in physical properties of the pericardial tissue, even in the same pericardial sac. Their research mapped out areas in individual pericardial sacs and tested those areas for fiber orientation, suture holding power, and thickness. In another paper by Sacks, *Bi-axial Mechanical Behavior of Fixed Bovine Pericardium,* Fifth World Biomaterials Congress, May-June 1996, the collagen fiber architecture within bovine. pericardial tissue was examined and various specimens were tested in a bi-axial tester. The results indicated that by presorting for uniform collagen fiber architecture, more uniform bio- pericardial specimens could be obtained for better controlled use in bioprosthetic applications. Finally, in another study, Zioupos, et al, *Anisotropic Elasticity and Strength of Glutaraldehyde Fixed Bovine Pericardium For Use In Pericardial Bioprosthetic Valves,* Journal of Biomedical Materials Research, Vol. 28, 1994, various tests were performed on fixed bovine pericardial tissue to determine the stress/strain behavior along various axes. The results suggest that leaflets can be made from fixed bovine pericardium possessing pronounced anisotropy in strength and stiffness along two orthogonal directions. In the leaflets circumferential direction, which bears most of the stress during function, the stiffer pericardium is desired, while in the radial direction, more flexible tissue is desired. Leaflets are thus cut from bulk tissue whose properties have generally been examined, and the leaflets categorized accordingly. Despite the extensive research into bulk tissue characteristics there remains a need for a more reliable method of selecting leaflets to insure maximum functional compatibility with the other leaflets in the dynamic operating environment of a prosthetic heart valve.

SUMMARY OF THE INVENTION

The present invention provides methods and apparatuses for selecting leaflets for use in producing multi-leaflet prosthetic heart valves. The selection of leaflets to be combined in a heart valve is based on grouping a plurality of leaflets by strain response to an applied load which is designed to simulate physiological pressures within the heart. A stress load sufficient to stress the leaflets within a high modulus region of their stress/strain characteristic is applied to each leaflet, and leaflets within a predetermined observed deflection range of each other are grouped together. In an exemplary embodiment, glutaraldehyde-fixed leaflets are stressed within at generally linear, high modulus region of the bulk tissue stress/strain curve, and the deflection measured for grouping the leaflets. In one embodiment, the strain response is observed relative to a deflection of bovine pericardium leaflets resulting from applying a load thereto, and two or three leaflets from a group of leaflets having deflections within 0.030 inches of each other are combined to form a prosthetic heart valve One aspect of the present invention is a method of selecting leaflets for an implantable heart valve, including providing a collection of similarly sized leaflets, applying a load to each leaflet, observing the resulting strain response, and sorting the leaflets based on their respective strain responses. The collection may be natural tissue leaflets which are chemically fixed prior to testing. The natural tissue leaflets may be made of bovine pericardium. In one embodiment, the load applied is sufficient to create an average stress in at least some of the leaflets of between 300 and 600 kPa. The load is preferably applied for a predetermined number of times prior to observing the strain response. Another aspect of the invention is a bioprosthetic heart valve manufactured with leaflets selected by the aforementioned method, wherein the number of leaflets selected may be three.

The present invention also provides a method of testing a leaflet for use in an implantable heart valve, including mounting the leaflet in a frame so that portions which are to be sutured in the valve are held stationary. A load is applied to the leaflet in a location adapted to simulate a point at which an average load is applied in the valve, and the resulting strain in the leaflet is sensed. The natural tissue leaflet typically defines a cusp and a coapting edge generally opposite the cusp, and the step of mounting may comprise holding stationary at least the cusp of the leaflet. The leaflet may be positioned in a framing assembly having a recess for receiving at least the edges of the cusps of the leaflet, and a cavity circumscribed by the recess. Moreover, the load may be applied by a mechanical deflector to an upper surface of the leaflet over the cavity. Preferably, the framing assembly includes an upper member and a lower member, the lower member having the recess and the upper member shaped to mate over the recess. The method further includes piercing the leaflet edges with needles extending between and supported from movement by the upper and lower members.

The present invention provides an apparatus for testing heart valve leaflets having a leaflet framing assembly including a holder with a recess for receiving a leaflet to be tested and a frame which cooperates with the holder to hold stationary the cusps of the leaflet. The apparatus includes a base having indexing structure for locating the framing assembly thereon, and a deflection assembly indexed with respect to the base and having a deflector mounted for movement above the framing assembly to contact the leaflet. The recess may be cusp-shaped, and the holder includes a cavity substantially surrounded by the recess over which the leaflet is suspended. The apparatus may further include structure adapted to hold stationary discrete points of the leaflet around the cavity. To secure discrete points of the leaflet around the cavity, the frame preferably includes a plurality of needles having their pointed ends downward, and the recess includes receptor holes for the needles, wherein the cusp of the leaflet is secured against movement at the discrete points defined by the needles.

BRIEF DESCRIPTION OF THE DRAWINGS

FIG. 10a is a graph showing a distribution of deflection values for a number of leaflets which have been previously grouped and categorized by droop characteristic, Category A;

FIG. 10b is a graph showing a distribution of deflection values for a number of leaflets which have been previously grouped and categorized by droop characteristic, Category B;

FIG. 10c is a graph showing a distribution of deflection values for a number of leaflets which have been previously grouped and categorized by droop characteristic, Category C.

DESCRIPTION OF THE EXEMPLARY EMBODIMENTS

The present invention involves testing individual leaflets for use in producing heart valves which, in its broadest sense, provides methods and apparatuses for obtaining and grouping the deflection response of individual leaflets in order to better sort or group them for later selection and combining with other leaflets to form a valve. Unlike prior art bulk tissue testing, the present invention characterizes individual leaflet response under loads similar to those the leaflets are subjected to under normal physiological conditions within the heart. Not only are the loads higher than previously used in tissue testing, but the leaflets are subjected to repeated loadings, which conditions the leaflet tissue, prior to observing a deflection. Although the bulk mechanical properties of tissue in general have been studied, prior art non-destructive tests of individual tissues already cut to leaflet shape have not been developed or utilized to group tissue leaflets for assembly into prosthetic valves.

An exemplary deflection testing apparatus, disclosed within the teachings of the present invention, closely simulates dynamic pressure on the individual leaflets with a mechanical deflector having a smooth, generally spherical tip on the end for repeatedly contacting a framed and supported leaflet at a pre-determined contact location. The leaflet is framed and secured around its periphery at a number of discrete points designed to simulate the lines of suturing that would retain the leaflet within an actual prosthetic heart valve. The invention should not be limited to the specific apparatus shown, however, and is intended to cover any equivalent apparatuses or methods which take individual leaflets and subject them to loading while measuring their deflection response. For example, an alternative apparatus contemplated as being within the scope of the present invention may apply a pressure to the leaflet, as opposed to a discrete or diffuse mechanical load.

Exemplary Deflection Tester Apparatus

Figure 1:
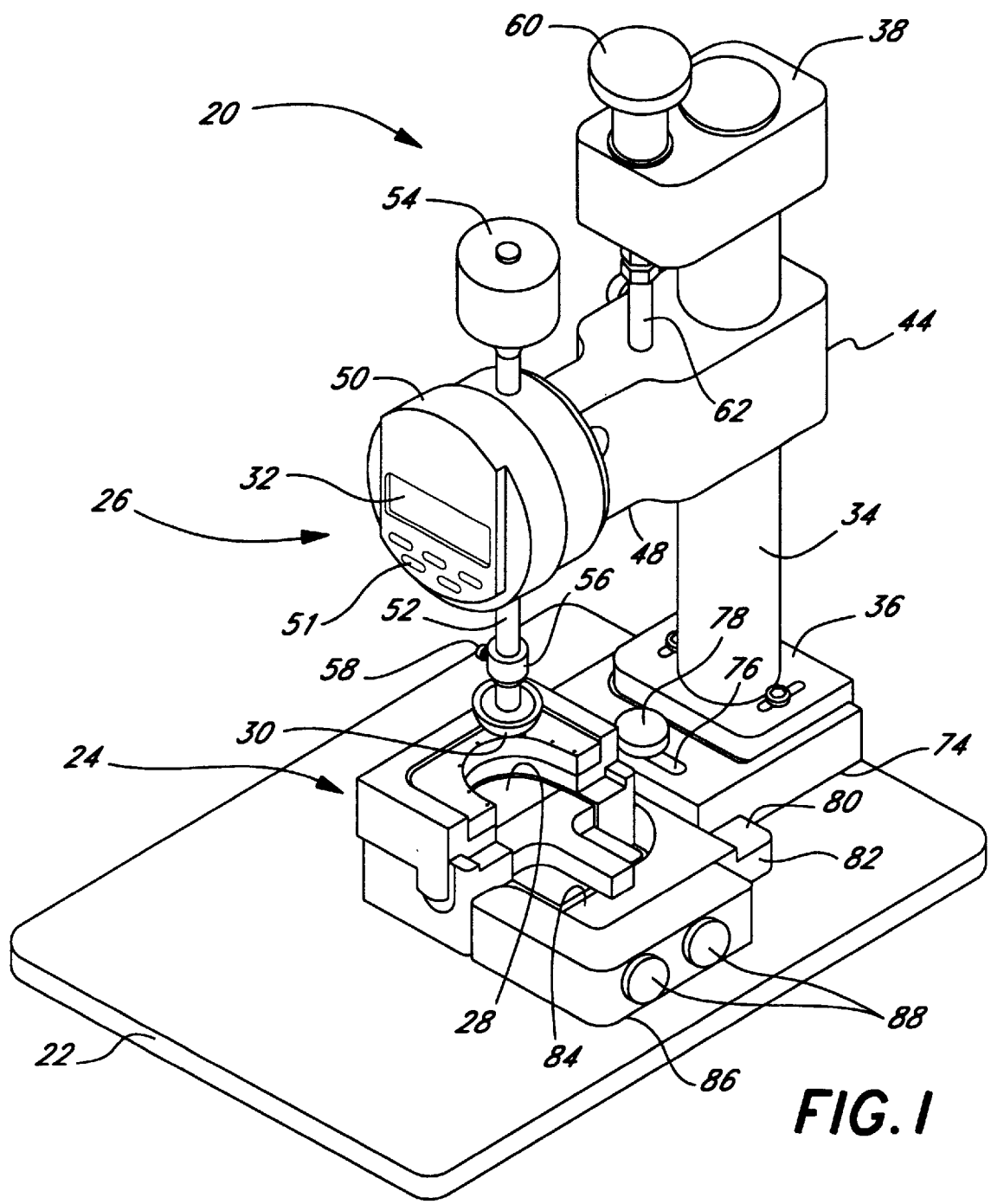
FIG. 1 is a front perspective view of an exemplary leaflet tester illustrating the principles of the present invention.
Figure 2:
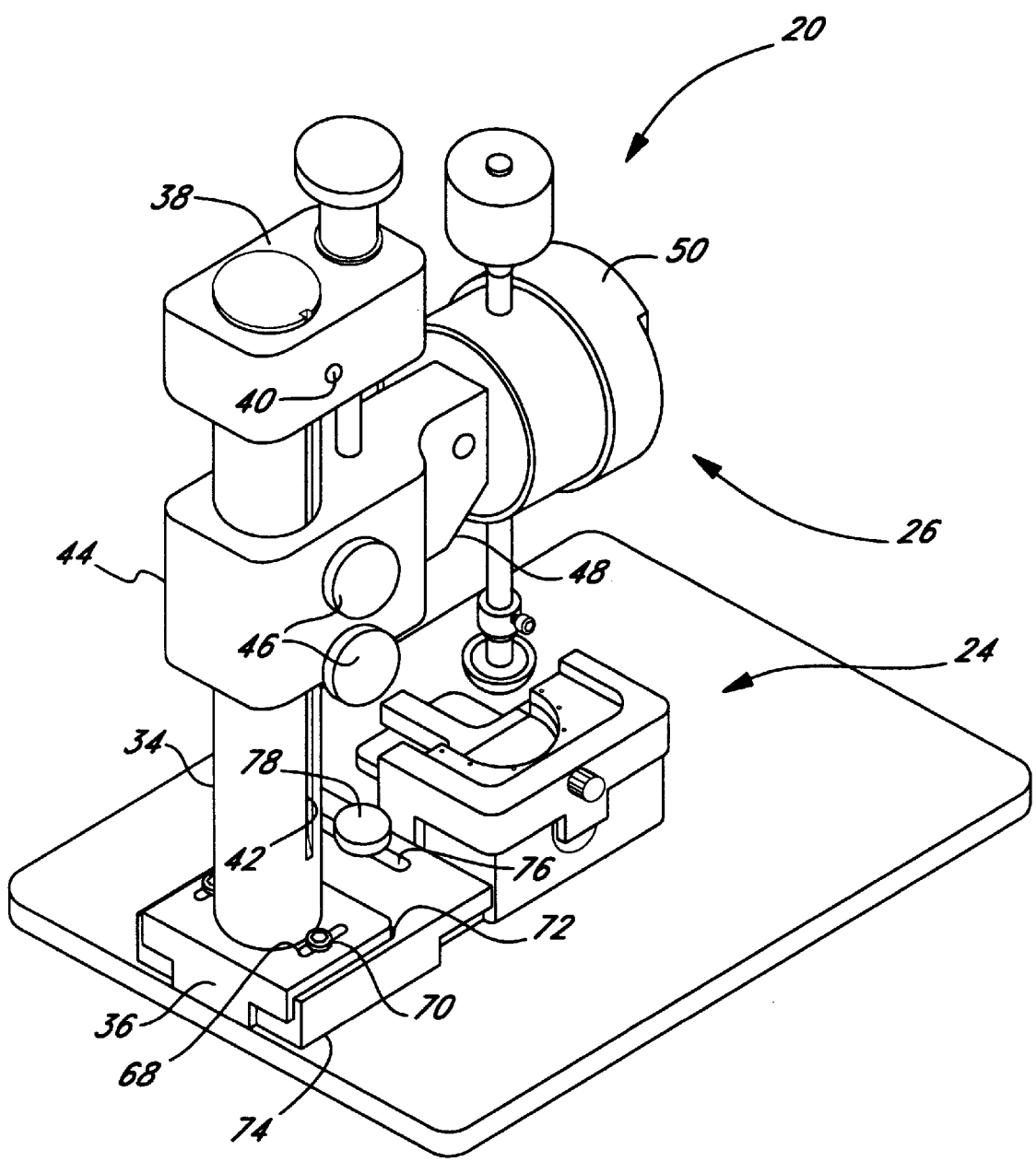
FIG. 2 is a rear perspective view of the leaflet tester of FIG. 1.

One particular embodiment of a leaflet deflection tester 20 for loading individual leaflets is shown in FIGS. 1 and 2. Referring to FIG. 1, the leaflet deflection tester 20 comprises a flat base 22 supporting a leaflet framing assembly 24 and a deflector assembly 26 thereabove. A leaflet 28 is shown mounted within the framing assembly 24 and a deflector 30 is positioned to apply a load to the leaflet to result in a deflection which can be read from display 32. For purposes of discussion, the display 2 faces in a forward longitudinal direction, and lateral left and right directions are defined from the perspective of looking at the display.

The deflector assembly 26 comprises a support post 34 vertically oriented with respect to the base 22 and attached thereto with a post holder 36. Referring to FIG. 2, at the top of the post 34, a cap 38 is vertically adjustable via a set screw 40 engaging a vertical groove 42 in one side of the post. An indicator carriage 44 is also vertically adjustable along the post and may be secured at various locations using a pair of carriage locking screws 46 which also engage the groove 42. A carriage arm 48 extends longitudinally forward from the post 34 and terminates in a position indicator 50 mounted thereto. Referring to FIG. 1, the position indicator preferably includes electronic circuitry and a digital readout 32, but may be of a variety of configurations, and the particular embodiment illustrated herein should not be construed as limiting. Control buttons 51 including a zero reset function are provided on the face of the indicator 50.

The position indicator 50 is generally centrally located above the leaflet framing assembly 24 and includes an indicator shaft 52, vertically passing therethrough and engaging position-sensing equipment within the indicator. That is, various known mechanical or electro-mechanical devices for sensing the displacement of a shaft within a housing are contemplated for this purpose and will not be described further herein. A mass 54 attaches to an upper end of the indicator 52 above the position indicator 50. At the lower end of the shaft 52, a collar 56 is fastened thereon via a locking screw 58. The collar continues downward and terminates in the aforementioned deflector 30.

The deflector assembly 26 further includes a means for vertically adjusting the position between the post cap 38 and the indicator carriage 44. A vertical adjustment knob 60 is mounted for rotation above a vertical axis through the post cap 38. The adjustment knob 60 engages a connecting rod 62 which extends between the post cap 38 and the indicator carriage 44. In one embodiment, the vertical adjustment knob 60 rotates a threaded nut within the post cap 38 which engages male threads on an upper end of the connecting rod 60 to cause its vertical displacement. The connecting rod 62 is preferably firmly connected to the indicator carriage 44 and thus turning the vertical knob 60 vertically displaces the indicator carriage 44. The use of the vertical adjustment knob 60 in calibrating and operating the tester 20 will be described below.

With reference still to FIG. 1, and, more particularly, to the rear perspective view in FIG. 2, the post holder 36 is formed as a monolithic T-shaped block, having a pair of overhanging edges through which longitudinally oriented adjustment slots 68 are provided. The slots 68 are provided on either lateral side of the support post 34 and receive locking bolts 70 which extend downward into engagement with a step 72 formed in a longitudinal adjustment bracket 74. The longitudinal adjustment bracket 74 can thus be adjusted longitudinally with respect to the post holder 36 and secured with the bolt 70.

On a front end of the longitudinal adjustment bracket 74, an overhanging portion includes a lateral adjustment slot 76 receiving a locking screw 78. Referring to FIG. 1, the locking screw 78 continues through the overhanging portion of the adjustment bracket 74 into contact with a step 80 formed in a lateral adjustment bracket 82 which is generally L-shaped, having a forwardly extending arm portion 84. An L-shaped clamp 86 is adjustable longitudinally with respect to the arm portion 84 and is fastened thereto with a pair of clamping screws 88. The combination of the adjustment brackets 74 and 82, and L-shaped clamp 86, index and secure the leaflet framing assembly 24 with respect to the support post 34 and, in turn, the position indicator 50.

Figure 3:
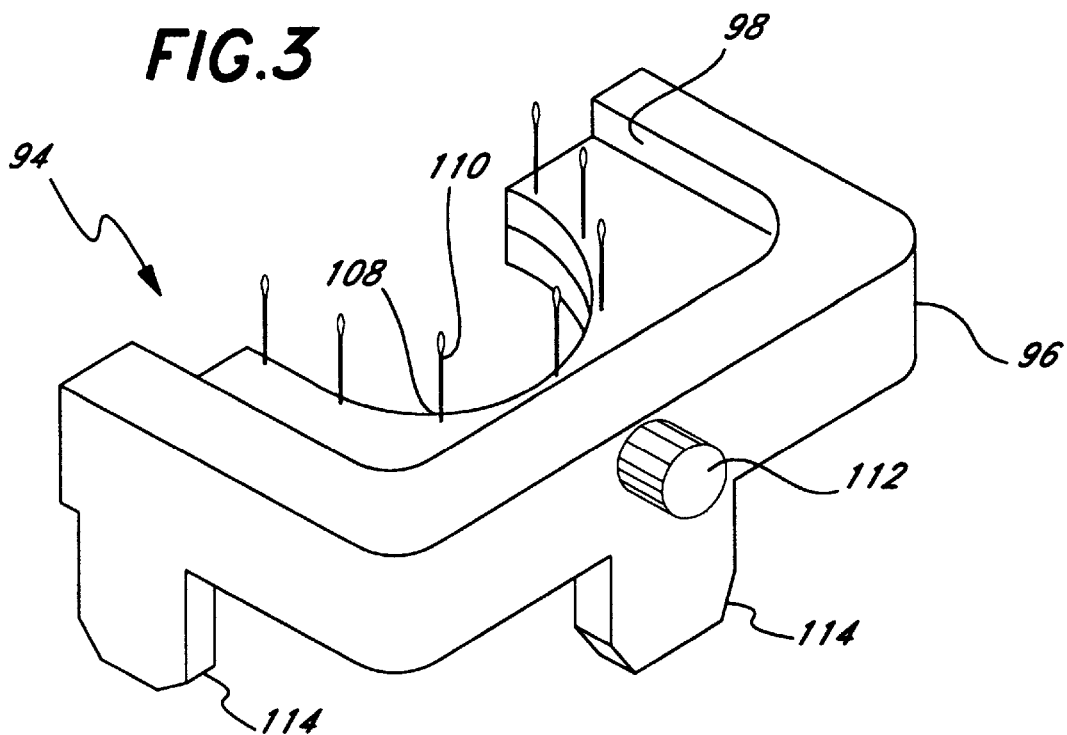
FIG. 3 is a perspective view of a leaflet mounting frame for use in the leaflet tester.
Figure 4:
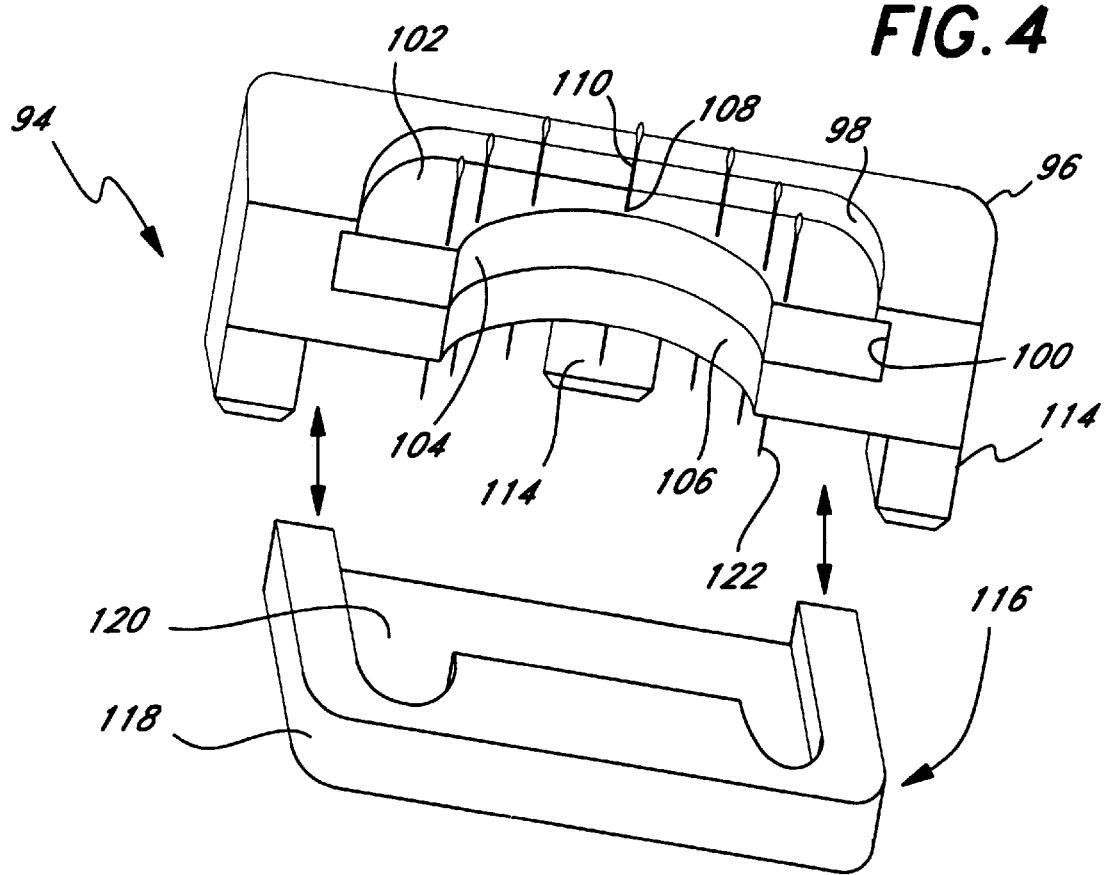
FIG. 4 is an exploded perspective view of the leaflet mounting frame and a needle calibration gauge for use therewith.

An upper framing assembly member or leaflet mounting frame 94, illustrated in FIGS. 3 and 4, comprises a generally rectangular shaped base 96, having an upper stepped recess 98 open to a front side of the rectangle. An undercut 100 is formed in the recess 98 to receive a plate-shaped needle clamp 102 therein. The needle clamp 102 includes a semi-circular cutout 104 in an edge facing toward the open edge of the recess 98. The cutout 104 conforms to a semicircular cutout 106 formed in the base 96. It should be noted that although the cutouts 104, 106 are described as generally semicircular, the particular shape of the leaflet 28 may be somewhat oval in shape, which may correspondingly alter the shape of the cutouts.

Both the base 96 and the needle clamp 102 include a plurality of registered, vertical through holes 108, arranged equidistantly around the semicircular cutouts 104 and 106. In a preferred embodiment, there are seven such through holes 108, arrayed at specific circumferential angles around the cutouts 104 and 106. The through holes 108 receive leaflet framing needles 110 which are vertically retained therein through the use of a needle clamp screw 112 threaded through a rear wall of the frame body 96 and into contact with the needle clamp 102.

The frame base 96 further includes a plurality of positioning tabs 114 depending downward therefrom. In the illustrated embodiment, there are three such tabs 114, two on left and right sides, respectively, of the frame base 96 and one on the rear side. With reference to FIG. 4, the tabs are utilized to orient a needle gauge or calibration member 116 under the cutouts 104 and 106. More particularly, the needle gauge 116 comprises a generally rectangular base 118 and a recessed pocket 120. The base 118 is guided between the two side tabs 114 and abuts against the rear tab of the mounting frame 94. In this orientation, the pocket 120 is positioned directly below all of the through holes 108 so that the needles 110 depend downward below the lower surface of the frame base 96, as seen at 122, only as far as the pocket. The needles 110 are inserted through the holes 108 into contact with the pocket 120, and then the needle clamp screw 112 is tightened to push the needle clamp 102 in a direction out of the recess 98 and create a compression against the needles 110. That is, the shear force exerted on the needles 110 by the through holes 108 in the frame base 96 and needle clamp 102 maintains the needles in the vertical position as calibrated by the needle gauge 116. Once the needles are calibrated to depend downward the same distance, the frame 94 is ready for use in the framing assembly 24.

Figure 5:
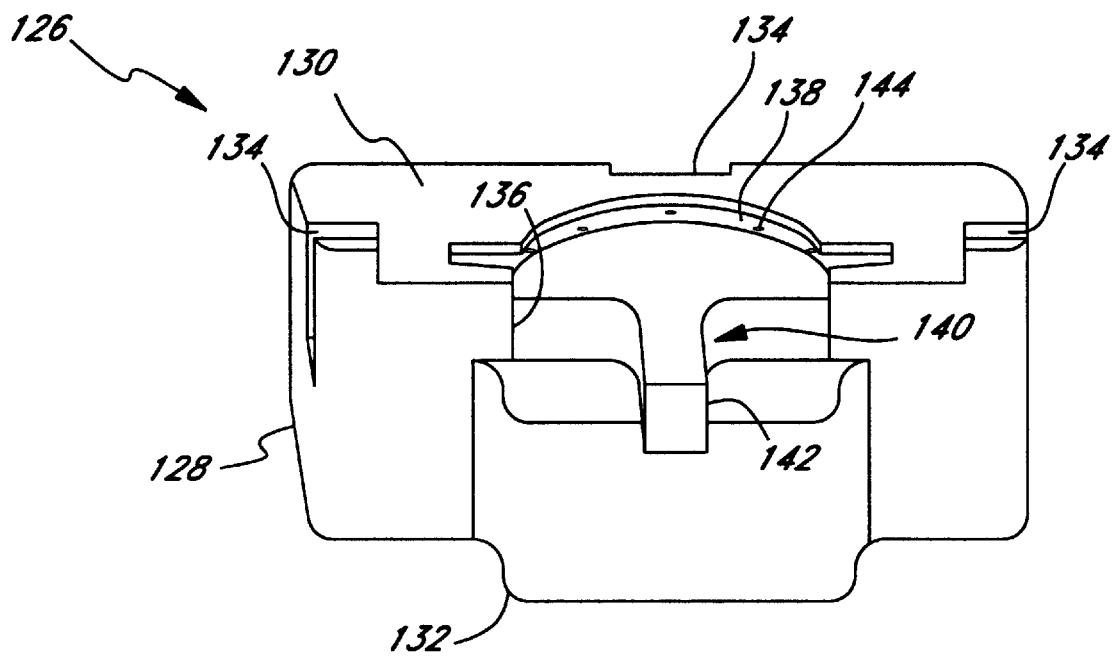
FIG. 5 is a perspective view of an exemplary leaflet holder for use in the leaflet tester.

FIG. 5 illustrates a lower framing assembly member or leaflet holder 126 comprising a. block-shaped body 128 having a flat lower surface adapted to rest on the base 22

Figure 6:
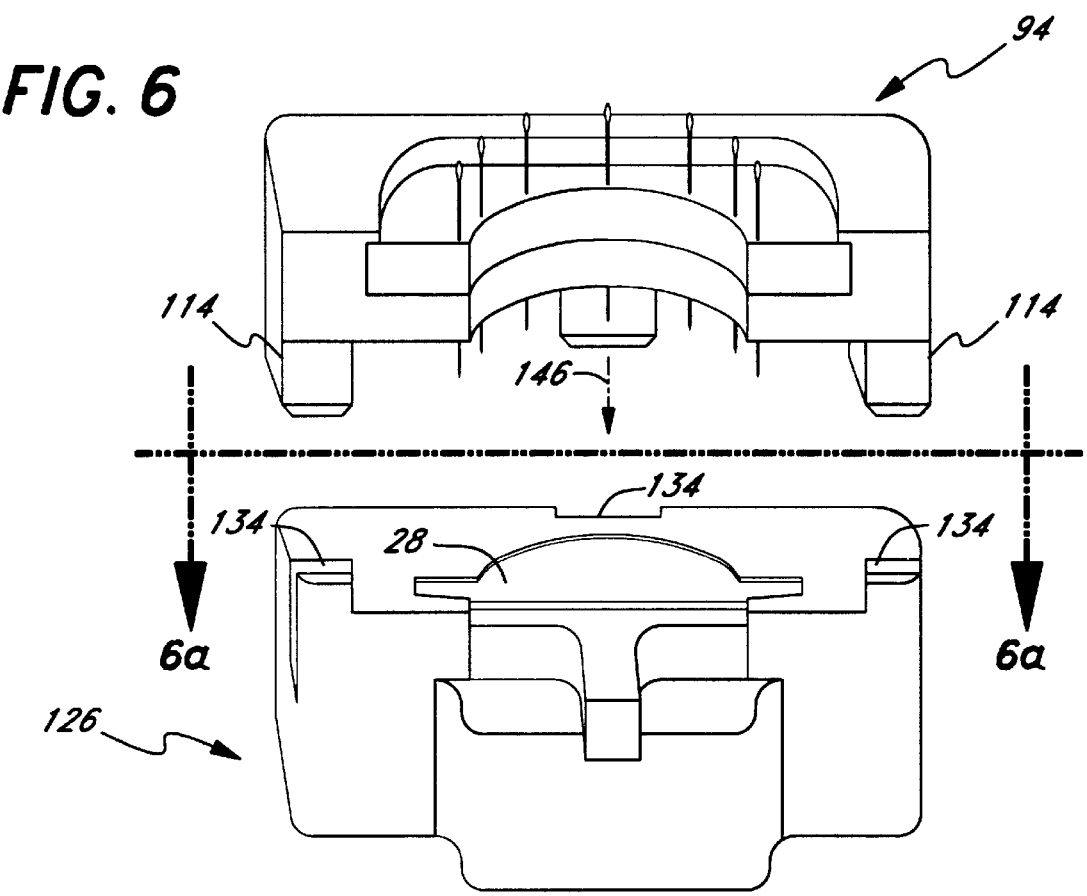
FIG. 6 is an exploded perspective view of the leaflet mounting frame over the leaflet holder, with a leaflet held therein.

(FIG. 1) and a flat upper platform 130. The body 128 is generally rectangular in shape and includes a rectangular base locator 132 projecting from a front side and shorter in height than the body 128. The outer edges of the body 128, other than the edge from which the base locator 132 extends, include positioning channels 134 opening to the platform 130. The positioning channels 134 receive the positioning tabs 114, previously described for the leaflet mounting frame 94, as best seen in FIG. 6, to locate the mounting frame with respect to the leaflet holder 126. The lower surface of the leaflet mounting frame base 96 is flat and is juxtaposed with the flat platform 130. In the center of the body 128, and opening toward the base locator 132, a cavity 136 is formed having a generally semicylindrical shape. A stepped leaflet edge recess 138 is formed in the platform 130 surrounding the cavity 136 and is sized and shaped to receive a leaflet, such as the leaflet 28 as shown in FIGS. 1 and 2.

Referring to FIG. 5, a paddle-shaped leaflet support 140 has a generally semicircular end which fits closely within the cavity 136, with a handle 142 extending outward from the cavity 136 and resting on a top surface of the base locator 132. The leaflet support 140 has a height which is identical to the height from the top surface of the base locator 132 to the elevation of the leaflet edge recess 138 so that the upper surface of the leaflet support 140 is in the same plane as the edge recess 138. The edge recess 138 further includes a plurality of needle receptor holes 144 sized and positioned in an array identical to the array in which the through holes 108 and associated needles 110 are positioned around the leaflet mounting frame 94. This arrangement allows the needles 110 to extend through the peripheral edge of the leaflet 28 into the receptor holes 144, thus holding stationary portions of the leaflet at the edge recess 138.

Figure 6A:
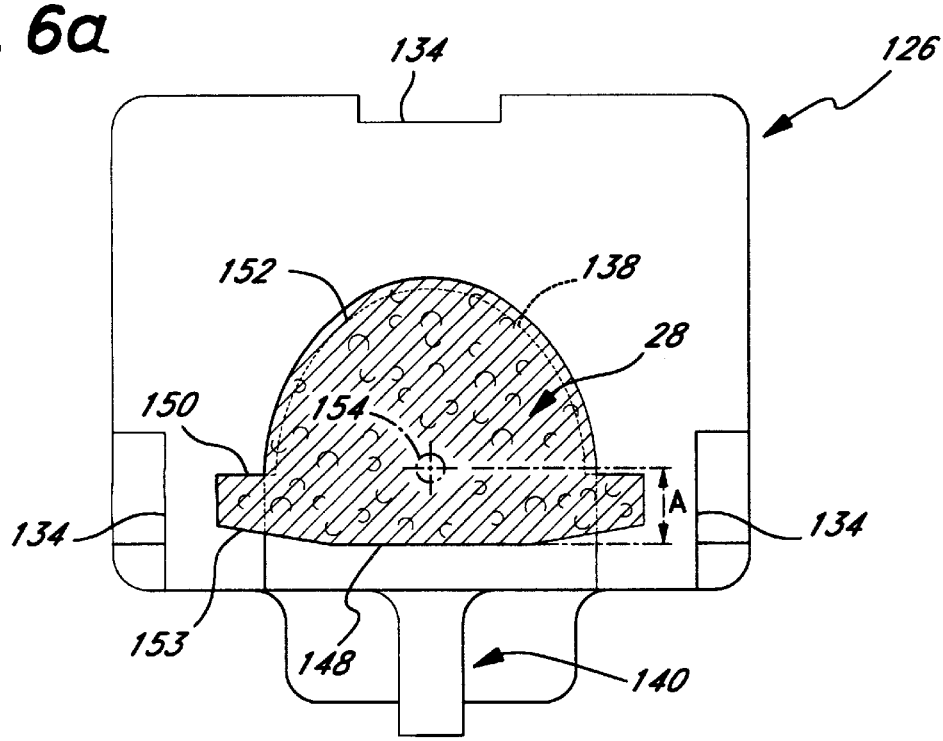
FIG. 6a is a top elevational view of the leaflet holder, with leaflet therein, taken along line 6a–6a of FIG. 6.

With reference to FIG. 6a, the leaflet typically includes a straight coapting edge 148 having opposed tab ends 150, and a generally semicircular cusp 152 therebetween and opposite the coapting edge. The tab ends 150 include angled sides 153 transitioning to the coapting edge 148. The edge recess 138 is sized and shaped to receive the cusp 152 and tabs 150 with the coapting edge 148 oriented parallel with but spaced from a front edge of the holder 126.

FIG. 6a also illustrates a point 154 at which an axis through the center of the deflector 30 intersects the leaflet 28. This point 154 will be referred to herein as the point of contact between the deflector 30 (FIG. 1) and leaflet 28, but in the exemplary embodiment the deflector is a relatively large diameter smooth hemisphere, and contacts the leaflet over a circular area to better simulate a distributed load and to help avoid stress risers. The point 154 is determined from a model of the stress distribution in the leaflet based on assumed forces applied to the leaflet in a human heart valve. The forces applied to the leaflet in a human heart valve originate from fluid pressures upstream and downstream of the valve, and the stress distribution is found from the leaflets' shape and boundary conditions (i.e., geometry of the lines of sutures attaching the leaflets in the valve). The point 154 is thus an idealized concentrated load point (or concentrated area) equivalent to the actual distributed pressure load.

The leaflet is symmetrical about an axis perpendicular to and bisecting the coapting edge 148, and is typically continuously sutured in an actual valve along the cusp 152, and thus the point 154 is desirably on that axis. The dimension "A" is the distance from the point 154 to the coapting edge 148 determined from the aforementioned stress distribution model. The dimension "A" will vary depending on the size and geometry of the leaflet, its thickness and bulk material properties, and the assumed stress distribution. It will be noted, however, that the point 154 is spaced from the coapting edge 148, which prevents undue tensile stresses between the deflector 30 and the points closest to the coapting edge at which the leaflet is held stationary in the framing assembly 24 (i.e., needles 110, as will be described below). The particular apparatus and methods disclosed, and the concentrated loading, requires that the point 154 be spaced from the coapting edge 148 to best distribute the tensile stresses between the deflector 30 and the stationary points at the leaflet periphery. Of course, those of skill in the art will recognize that a more accurate test setup with actual suturing around the cusp 152 and a pressure loading over the surface of the leaflet could be substituted within the scope and teaching of the present invention, and the presently illustrated test setup is an approximation driven by practical manufacturing considerations.

Figure 7:
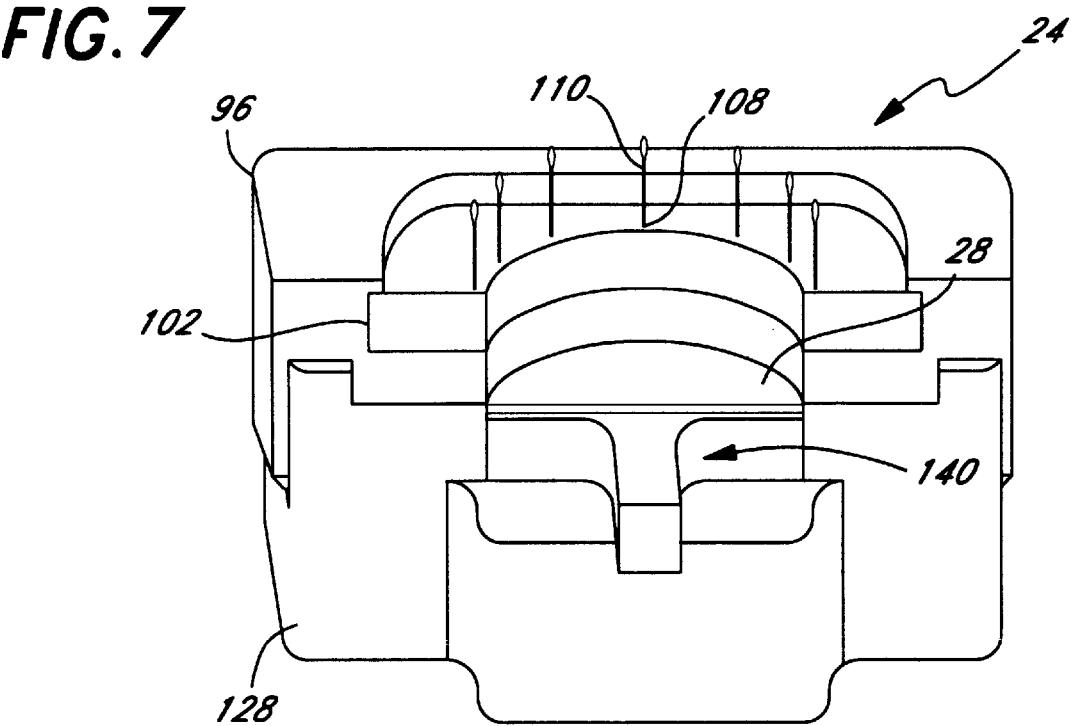
FIG. 7 is an assembled perspective view of a leaflet framing assembly comprising the leaflet mounting frame, and leaflet holder.

The interaction of the leaflet mounting frame 94 with the leaflet holder 126 will be explained with reference to FIG. 6 and 7. As mentioned, the positioning tabs 114 fit within the positioning channels 134 to orient the mounting frame 94 with respect to the leaflet holder 126. The registration between the tabs 114 and channels 134 insures that the needles 110 in the through holes 108 in both the base 96 and needle clamp 102 of the mounting frame 94 align with the needle receptor holes 144 in the leaflet holder 126. The assembly arrow 146 illustrates the movement of the mounting frame 94 when coupling to the leaflet holder 126. In art anticipated alternative embodiment, the mounting frame 94 will be hingedly or otherwise pivotally coupled to the holder 126, with the final relative movement being vertical to avoid skewing the needles within the receptor holes 144.

The leaflet 28 is pre-positioned so that its outer edges conform to the shape of the leaflet edge recess 138, and the middle portion is supported by the leaflet support 140. The needles 11 extending down below the leaflet mounting frame 94 thus pierce and pass through the tissue of the leaflet 28 and extend into the receptor holes 144. In a heart valve, the cusps 152 of each leaflet are supported by a wireform, and the coapting edges 148 remain free to cooperate with the coapting edges of the other leaflets. The framing assembly 24 thus closely simulates the static points of attachment so that the stress distribution, and accompanying deflection response, in the leaflet 28 is as near to the actual distribution as possible. The needles 110 hold stationary peripheral portions of the leaflet 28 to approximate an actual line of sutures peripherally securing the leaflet within a heart valve. Furthermore, the lower surface of the mounting frame base 96 rests on the upper surface of the platform 130. In this regard, it is important to note that the leaflet 28 is preferably not compressed, or only lightly compressed, by the weight of the mounting frame 94 because it is positioned within the recess 138. The final assembled leaflet framing assembly 24 is illustrated in FIG. 7.

Figure 8A:
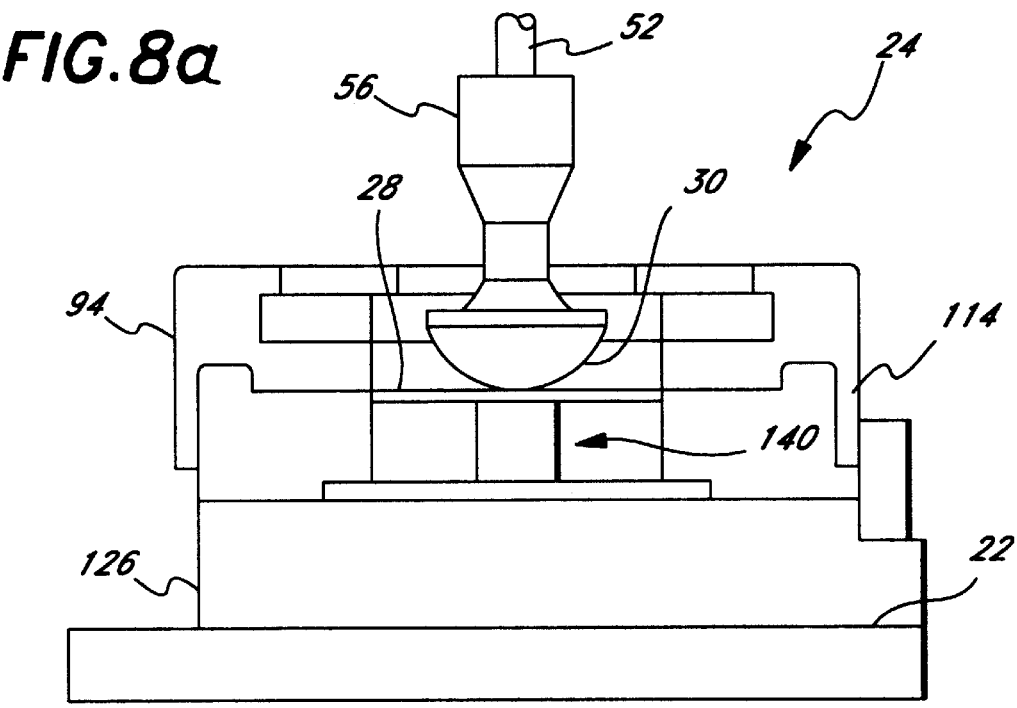
FIG. 8a is an elevational view of a deflector in contact with a leaflet to be tested and mounted within the framing assembly prior to a deflection test.
Figure 8B:
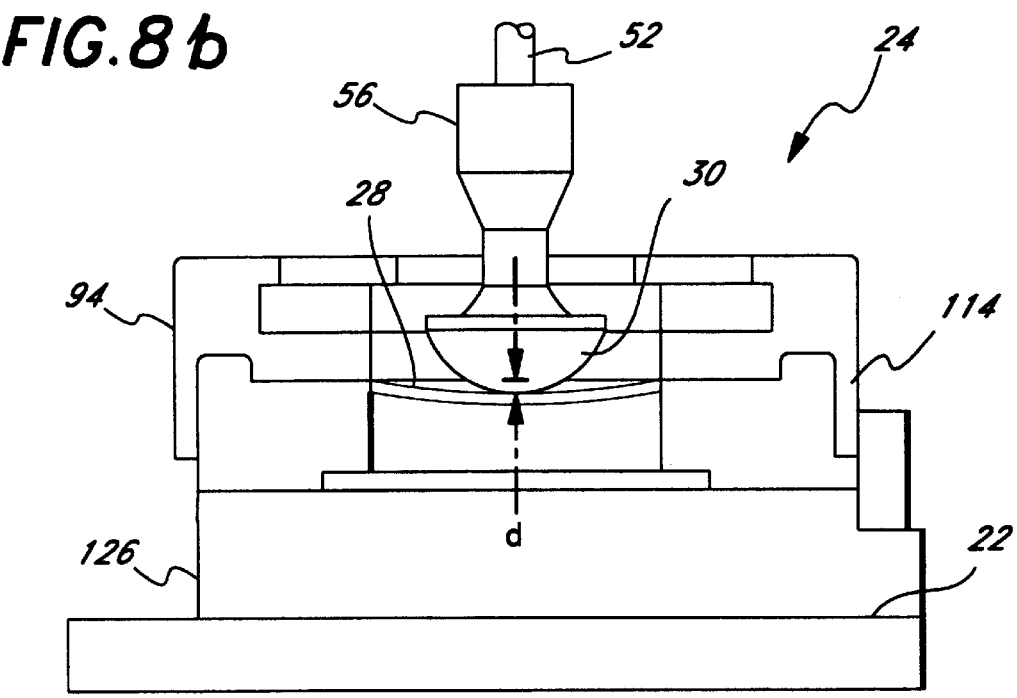
FIG. 8b is a front elevational view of the framing assembly with a leaflet support removed and the deflector deflecting a leaflet.

FIGS. 8a and 8b illustrate two positions of the deflector 30 during a leaflet deflection test. The leaflet 28 is mounted in the framing assembly 24 with the leaflet support 140 supporting the leaflet 28 from underneath in a plane at the same elevation of the leaflet edge recess 138, and thus the leaflet 28 does not bend or sag in its mid-portion. The deflector 30 is lowered into a position just contacting the top of the leaflet 28, as shown in FIG. 8a, prior to a deflection test. Subsequently, the leaflet support 140 is removed from underneath the leaflet 28, and the indicator shaft 52 is allowed to drop as in FIG. 8b, thus causing the deflector 30 to displace the leaflet 28 until an equilibrium is reached. The equilibrium depends on the framing geometry, the size of the mass 54 (FIG. 1), and the stress/strain characteristics of the leaflet 28. The total deflection of the leaflet at the point of contact with the deflector 30 is illustrated in FIG. 8*b* by the dimension "d". As described below in the Exemplary Test Assembly section, an approximate measurement of the true deflection "d" is made by disregarding the relaxed thickness of the leaflet being tested for simplicity of calibration of the apparatus and method.

Preferably, the deflector 30 is a relatively large diameter smooth hemisphere so that the load imposed on the upper surface of leaflet 28 is somewhat distributed. The deflector 30 is made of a biocompatible material, such as a plastic, and preferably a thermoplastic. Other variations of deflector 30 are envisioned and the present invention should not be construed to be limited to the illustrated embodiment. For example, a more uniformly distributed load such as a pressure load may be imposed upon the leaflet 28 and the subsequent deflection measured. In all cases, the aim is to closely simulate the conditions experienced by the leaflet 28 in an actual heart valve. Indeed, it would be desirable to load test leaflets after being installed on a heart valve wireform and support ring. However, even if such a test could be accurately configured, it would be difficult to test individual leaflets within a three leaflet prosthetic valve, for example. Furthermore, once the valve has been constructed, many of the benefits of the leaflet selection process are rendered moot. That is, the primary consideration is finding similar leaflets to combine within a single heart valve. A secondary consideration, which is not insignificant, is being able to select a leaflet prior to construction of the valve to reduce manufacturing time and expense. Construction of a heart valve involves many intricate steps of sewing leaflets together and to the wireform and surrounding fabric covering. The work must be done by highly skilled technicians and thus testing of individual leaflets within fully constructed valves is prohibitively expensive, although not outside of the scope of the present invention.

The present invention thus seeks to provide a selection method for individual leaflets prior to construction of a heart valve which most accurately predicts the ultimate mechanical response of each leaflet within the constructed valve and ensures optimum performance in coaptation with the other leaflets. To that end, the presently illustrated test apparatus 20 is believed to closely simulate the forces and stresses imposed on the leaflet during use, in a relatively easy to set up and operate environment. Because of the modular nature of the test apparatus 20, repeatability of tests for various sizes of leaflets is enhanced. That is, the leaflet holder 126 is sized for a particular diameter of leaflet, and a number of leaflet holders having different leaflet edge recesses 138 may be provided for different sized leaflets. The external dimensions of the leaflet holder 126 remain the same so that it may be indexed within the aforementioned brackets on the platform 22 (FIG. 1) and the same deflection assembly 26 is utilized. Concurrently, the leaflet mounting frame 94 may be provided in a variety of sizes to cooperate with different sized holders. An additional advantage is the relatively small size and portable nature of the tester 20. The platform 22 may be set up on assembly lines, laboratory tables, and even desktops.

Exemplary Test Assembly

The steps in preparing the exemplary tester apparatus 20 for use will now be described with respect to the drawings. First of all, the equipment is cleaned to remove any particulate matter and dirt adhered thereto. The test equipment is then sterilized through a process including a bio-burden reduction process (BREP) well known in the art.

With reference to FIGS. 1 and 2, the post cap 38 is first secured on the post 34 by tightening the set screw 40. The locking screws 46 are loosened to allow the carriage 44 to freely move vertically on the post 34. Additionally, the locking bolts 70, locking screws 78, and clamping screws 88 are loosened. Prior to installing the leaflet framing assembly 24, the framing assembly 24 must be indexed under the deflector assembly 26. To accomplish this, an indexing tip (which is not shown) is fastened to the lower end of the indicator shaft 52 in place of the collar 56 and deflector 30. The indexing tip on the lower end of the indicator shaft 52 fits through an indexing hole (not shown here) within the cavity 136 formed in the leaflet holder 126. The indexing hole allows the indexing tip to contact the platform base 22. Once the indexing tip has contacted the base 22, the carriage locking screws 46 are tightened to locate the carriage 44. As the indexing hole is sized just large enough to receive the indexing tip, the leaflet holder 126 is located in its proper position with respect to the position indicator 50. That is, the vertical axis of the indicator shaft 52 is positioned at the precise location with respect to the leaflet holder 126 so that the deflector 30, when eventually installed, will contact the leaflet 28 in the proper position.

The longitudinal adjustment bracket 74 and lateral adjustment bracket 82 are then manipulated to contact the framing assembly 24 under the deflector assembly 26. The longitudinal adjustment bracket 74 and lateral extending portion of the lateral adjustment bracket 82 are displaced to contact the associated sides of the leaflet holder 126, and the arm portion 84 contacts the end of the base locator 132. The locking bolts and locking screw 78 are tightened. The carriage locking screws 46 are then loosened and the vertical adjustment knob 60 manipulated to raise the carriage 44 upward. The indexing tip is removed.

The correct size deflector 30 is chosen depending on the size of the leaflet 28 to be tested. The collar 56 of the deflector 30 is attached to the lower end of the indicator shaft 52 via the locking screw 58. Next, the proper size mass 54 is selected for the leaflet 28 to be tested. In this regard, a single mass for a particular size of leaflet 28 is preferred, although different masses may be used on the same leaflet for a variety of deflection results. The mass 54 must be selected so as not to over stress the leaflet 28 being tested. Thus, for example, stress loading for a glutaraldehyde-fixed pericardial tissue leaflet within a mitral valve is up to 1,000 kPa. For this application, therefore, the mass 54 should be chosen so that the stress imparted to the leaflet 28 is no greater than 1,000 kPa.

At this point, the position indicator 50 is calibrated. With the leaflet support 140 in position, the position indicator 50 is reset so that the display 32 reads zero, using one of the control buttons 51. The carriage locking screws 46 are then loosened and the entire position indicator 50 is lowered using the vertical adjustment knob 60 on the top of the post cap 38. The carriage 44, along with the position indicator 50, is lowered until the deflector 30 contacts the upper surface of the leaflet support 140. The vertical adjustment knob 60 is further turned to lower the position indicator 50 while the indicator shaft 52 remains stationary until the display 32 reads a deflection of between approximately 0.390" and 0.410". Then the carriage locking screws 46 are tightened to lock the position indicator 50 in place.

The display 32 is then again set to a zero reading, using one of the control buttons 51.

This sequence ensures that the deflector 30 can drop a sufficient distance below the level of the leaflet support 140 to ensure the leaflet under test is properly stressed (i.e., not understressed). That is, a proper deflection reading is desirably obtained within a nearly linear, high modulus region of the particular leaflet stress/strain curve, prior to reaching the yield stress, as described below with reference to FIG. 11. In general, the optimum stress level is first approximated, and the mass and total allowable deflection selected accordingly from that approximation to result in stress in a linear region of the tissue stress/strain curve.

It should be noted that the leaflet deflection is measured from a zero datum of the top of the leaflet support 140, and the thickness of the particular leaflet is disregarded. The leaflet thickness is relatively small in comparison to the deflection, and the ultimate test results are used to compare leaflets, so the slight inaccuracy from not taking the leaflet thickness into account applies to all of the leaflets, and is thus rendered even less important. Thus, the dimension "d" indicated in FIG. 8b is the true deflection, while the deflection actually measured is off by the relaxed thickness of the leaflet being tested, and is a close approximation of the true deflection.

The next step in the test preparation process is to secure the leaflet 28 within the framing assembly 24. First, the leaflet mounting frame 94 is assembled by inserting the needle clamp 102 in the base 96. As mentioned previously, the appropriately sized base 96 and needle clamp 102 are chosen for the particular leaflet 28 being tested. The needles 110 are inserted into the through holes 108, until their tips just extend beyond the lower surface of the base 96 as seen in FIG. 4. Of course, throughout this operation, the needle clamp screw 112 is loose to remove any shear force between the needle clamp 102 and the base 96.

As shown in FIG. 4, the leaflet mounting frame 94 is then positioned over the needle gauge 116 on a flat surface and the needles 110 allowed to drop until their lower tips contact the upper surface of the pocket 20. At this stage, the needle clamp screw 112 is tightened to apply a shear between the needle clamp 102 and the base 96, which holds the needles 110 in their calibrated elevation. The needles 110 are individually pulled to insure that they are tightly held in the proper position and if any of the needles move, the needle clamp screw 112 is recalibrated and tightened further. Before placement of the leaflet 28 within the leaflet holder 126, the leaflet mounting frame 94 is first positioned over and mated with the leaflet holder to insure that the needles 110 register with and extend freely into the receptor holes 144. The mounting frame 94 is then removed from the leaflet holder 126.

The leaflet support 140 is then installed in the cavity 136 of the leaflet holder 126, and the leaflet 28 to be tested positioned on the leaflet support so that its peripheral edges conform to the appropriately sized leaflet edge recess 138. The mounting frame 94 is then brought vertically over the leaflet holder 126 and displaced downward so that the needles 110 pass through the tissue of the leaflet 28 and into the receptor holes 144. In its assembled state, as shown in FIG. 7, the lower surface of the base 96 rests on the upper surface of the platform 130, with the positioning tabs 114 oriented in the positioning channels 134. In this arrangement, therefore, the peripheral edges of the leaflet are not pinched or otherwise compressed between the framing assembly halves. This helps reduce damage to the leaflet which may be assembled in a prosthetic valve and implanted for use in a patient.

The leaflet framing assembly 24 with leaflet 28 mounted therein is then placed back into its previously indexed position under the deflector assembly 26. The L-shaped clamp 86 is brought into contact with the side of the base locator 132, and the clamping screws 88 tightened to secure the framing assembly 24 on the base 22.

At this point, the deflector 30 is elevated manually with the position indicator 50 remaining stationary. The deflector 30 is then placed gently on the top of the leaflet 28 by manually lowering the shaft 52. The leaflet support 140 is then removed carefully from underneath the leaflet 28 which is allowed to deflect under the weight of the mass 54. The deflector 30 is elevated away from contact with the leaflet 28, and the test is repeated several times to insure correct readout. Preferably the leaflet 28 is deflected five times, and the readouts of the fourth and fifth deflections are then recorded.

Upon removal of the leaflet mounting frame 94, the leaflet 28 should stay with the frame by virtue of the needles 110 piercing the leaflet tissue. If all seven of the needle tips are visible through the leaflet tissue, then the leaflet 28 is removed from the mounting frame 94 by loosening the needle clamp screw 112 and pulling the needles 110 out from above. The leaflet 28, if useable, is then placed in its particular deflection grouping and stored for later combination with similar leaflets to produce a heart valve.

If any of the needles 110 are not visible through the tissue, then the mounting frame 94 is reinstalled onto the leaflet holder 126. After removing the mounting frame 94 once again, the needle tips should be visible through the leaflet 28. When all the needle tips are visible through the leaflet 28, the mounting frame 94 is replaced on the leaflet holder 126 and one or more deflection tests are repeated. The data from the second set of deflection tests are then used to select and classify the leaflet for later grouping with other leaflets. After this second test, the leaflet 28 is removed from the mounting frame 94 and placed in its particular deflection grouping.

Exemplary Tissue Selection Methodology

Studies in the prior art have demonstrated there can be a significant variation in the stress/strain curves from specimen to specimen of pericardial tissue. Tests have also demonstrated that typical stress loading of glutaraldehyde-fixed pericardial tissue results in varying strains for different tissue samples, even from the same pericardium sac. Moreover, leaflets may experience localized stresses within a mitral valve of up to 1,000 kPa, with a typical high average range of between 500 and 600 kPa. Previous studies have shown that the average stress/strain curve of leaflet tissue material non-linearly increases until a particular stress is reached after which the curve is approximately linear (the tissue stretches significantly more at low loads). In general, tissue is significantly stiffer in the high stress region, and is more flexible at low stresses.

Figure 11:
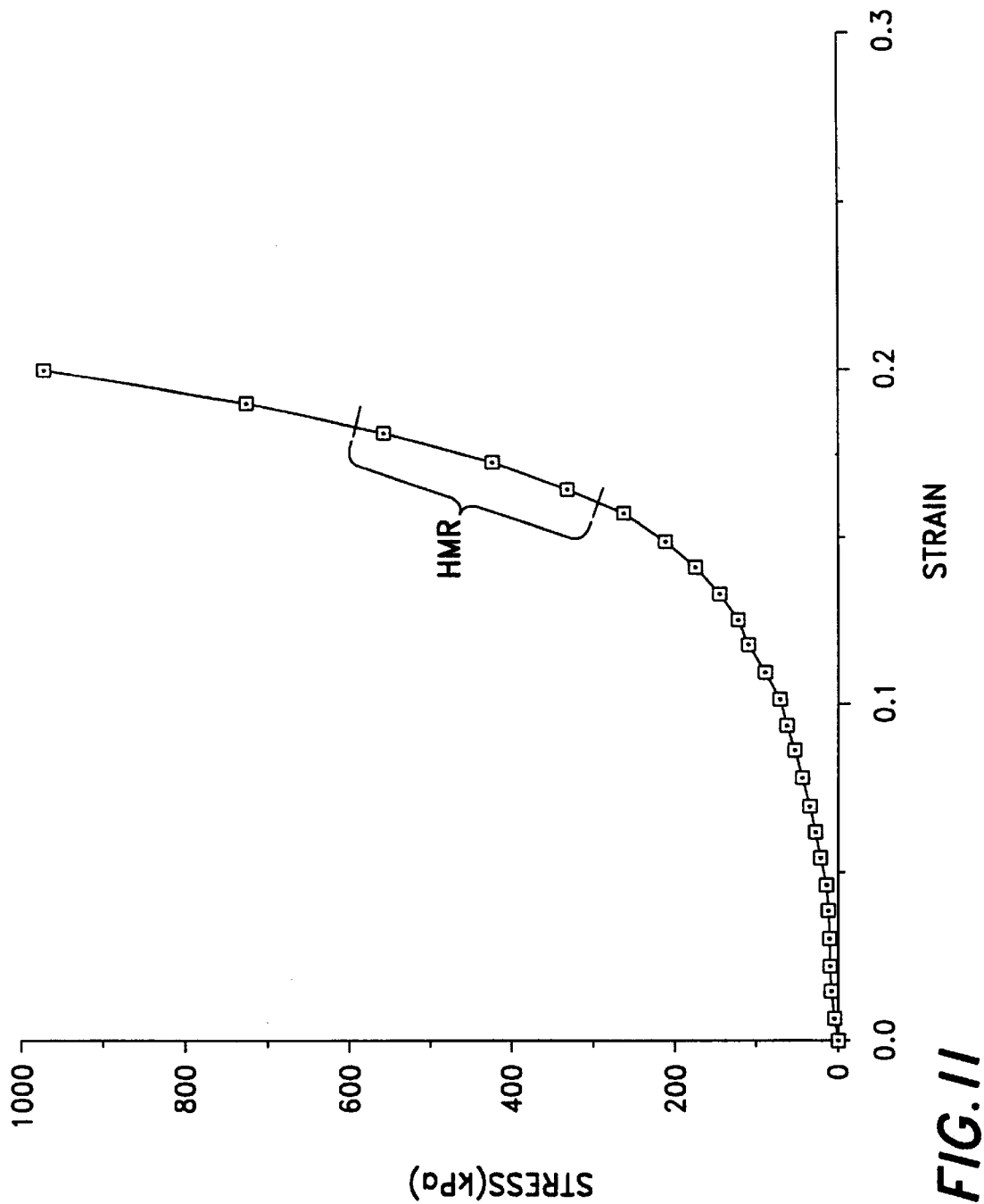
FIG. 11 is a graph illustrating a typical stress-strain curve for pericardial tissue.

FIG. 11 illustrates a typical stress-strain curve for pericardial tissue. It will be understood that the curve is exemplary for a particular tissue fixed in a particular way. Other tissues may respond differently, but the trends shown are generally seen in fixed bovine pericardium tissue. The curve shows a low elastic modulus of the tissue at low stresses under about 300 kPa, and an increasing modulus at higher stresses. The curve is generally linear above about 300 to 600 kPa. For purposes of discussion, a high modulus region (HMR) of the curve is shown in FIG. 11 within which the stress/strain curve is generally linear. The HMR is an approximation of an average high stress range within a particular fixed bovine pericardium leaflet in an implanted heart valve. This approximate information can be combined with knowledge of the operating conditions and valve size to design an appropriate deflection test method. That is, the bulk tissue stress/strain curve along with the valve size and assumed loading and boundary conditions can be combined to predict a stress distribution in the leaflet. The size of the mass 54 in the illustrated exemplary test apparatus 20 (FIG. 1), for example, is then selected to stress the leaflet into the HMR of the tissue. Understressing the leaflet during the test may not obtain optimum results, and over-stressing the leaflet may damage it. Thus, for example, a preferred stress level applied to glutaraldehyde-fixed pericardial tissue leaflets for a 29 mm CEP valve in the tester apparatus 20 has been found to be in the HMR of between 300 and 600 kPa.

The present tissue deflection test addresses the observed variation in resulting strain in tissue leaflets when the applied load is similar to pressure loading under physiological conditions. As mentioned previously, localized stresses on a leaflet in use may reach 1,000 kPa. Testing of leaflets within the tester 20 is preferably accomplished using a significantly lower stress level:, while still sufficiently deflecting the leaflet in the linear stress/strain region for useful results. Empirical testing or finite element stress analysis on specific leaflet material is desirably used to predict the probable stress-strain relationship of individual leaflets. This preliminary testing or analysis is then used to design the proper deflection test method, as described herein.

The particular testing stress level, however, is also affected by the type of test configuration. The needles 110 secure the edges of the leaflet 28 in a uniform circumferential array which simulates the sutures which attach the leaflet cusp within a heart valve prosthesis., In particular, the cusp 152 of the leaflet 28 is held stationary at discrete points defined by the needles 110, while the coapting edge 148 remains free. The number of needles 110 should be sufficient to simulate this edge connection of the leaflet in use, but not be too numerous as the needles pierce through the tissue of the leaflet. Therefore, between at least five and nine, and preferably at least seven needles 110 as shown are adequate for a uniform framing configuration of the leaflet without creating an inordinate number of holes therein. As the load is applied by the deflector 30 the stress distribution within the leaflet 28 will not be completely uniform because the leaflet is only held at discrete locations. Therefore the load applied must be carefully gauged, so as not to create undue levels of stress concentration in and around the points at which the needles pierce through the leaflet tissue. The stated range of between 300 and 600 kPa for glutaraldehyde-fixed pericardial tissue leaflets has been determined to be suitable when using seven needles as shown. Of course, other arrangements for framing the leaflet are possible, such as using more than seven needles, and the stress range may be appropriately modified. Further, the stress range is not determined solely with reference to the leaflet holding arrangement. Those of skill in the art will recognize the exemplary test apparatus is an attempt to simulate true stresses imposed on the leaflet, with certain tradeoffs, including simplifying the test apparatus and minimizing the number of needles used.

The mass 54 for a 29 mm CEP leaflet is chosen to be approximately 100 g to set up stress levels of between 300 and 600 kPa in the leaflet. The mass 54 for other size valve leaflets are scaled from the 100 gram load used for the 29 mm valve leaflet, as seen in Table I.

TABLE I

| Valve Leaflet Size | Deflection Load (g) |
|---|---|
| 25 mm | 74 |
| 27 mm | 87 |
| 29 mm | 100 |
| 31 mm | 112 |

Additional testing may be performed to insure that the appropriate mass 54 selected for various valve size leaflets imparts a stress in a generally linear region of the tissue stress/strain curve. One example of such testing is to use an Instron tensile test tester in place of the position indicator 50. The Instron Tensile tester can be used to vary the load on the leaflet 28 and a series of stress/strain curves can be generated for each leaflet size. Based on these test results, the minimum load on the tissue leaflets for all sizes to ensure that the stress/strain response is in the linear regime is approximately 60 grams.

Other means of categorizing leaflets may be used in conjunction with the presently described deflection test. For example, selection of individual leaflets to be grouped with other leaflets in a heart valve has been accomplished by the assignee of the present invention using a so-called "droop" test of the leaflets. That is, the leaflets are cantilevered over the end of a rod, or other structure, and the droop of the leaflet for different lengths of extension is observed. The droop test can thus be generally termed an intrinsic loading test, wherein there is no applied load and the leaflet deflects solely under its own weight. The droop test is used to categorize leaflets, so that leaflets with similar droop characteristics can be put together for assembly into a heart valve in an attempt to improve leaflet cooperation and coaptation. The droop test in combination with the presently described deflection test is particularly useful in grouping individual leaflets with similar characteristics for assembly into a multi-leaflet valve.

Figure 9:
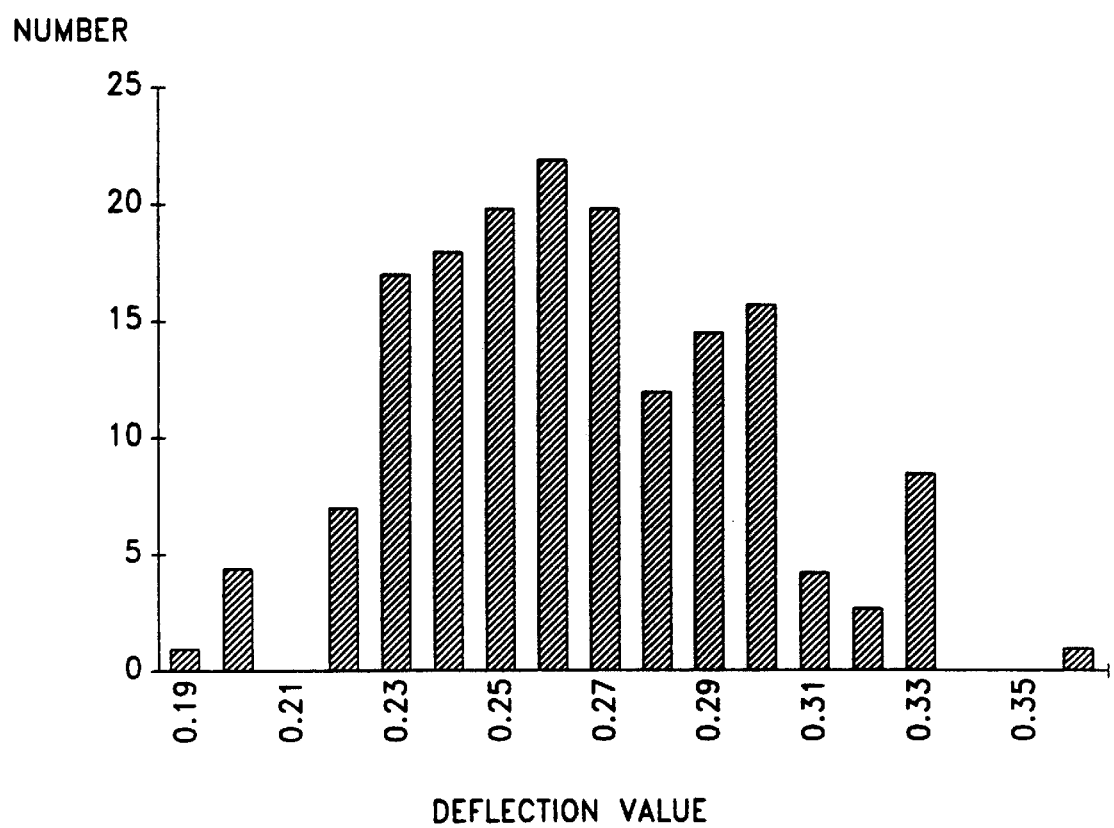
FIG. 9 is a graph showing tissue deflection values for a plurality of 29 mm CEP mitral valve leaflets.

Results for loading of leaflets for use in various size valves is given in FIG. 9. After the leaflets were deflected five times in succession to account for conditioning or change in the Young's modulus, a final deflection comprising the last observed deflection or an average of the last two observed deflections were recorded. FIG. 9 shows the distribution of deflection values from the tissue deflection test. The deflection values for the leaflets measured ranged from 0.19 to 0.36 with the majority grouped between 0.23 and 0.30.

To illustrate the effectiveness of the methods and apparatuses of the present invention relative to conventional tissue categorizing techniques, the droop test and tissue deflection test of the present invention were applied to 169 leaflets. The leaflets tested for deflection response in FIG. 9 were then categorized by droop value. FIGS. 10*a*, 10*b*, and 10*c* show the population of leaflets categorized by letters A, B and C based on droop characteristic. In general, the leaflets from Group A had the lowest deflection values with Group B somewhere between Group A and Group C. There is significant overlap of deflection values between categories A, B, and C.

In an exemplary embodiment, the deflection test described herein is first used to categorize a number of similarly shaped leaflets into subgroups, such as is shown in FIG. 9. Subsequently, a droop test is performed on a subgroup of leaflets within a predetermined deflection range, and only leaflets within an acceptable droop range from that subgroup are combined into a prosthetic heart valve.

Alternatively, the droop test may be performed first to obtain a number of subgroups, one or more of which is then deflection tested to arrive at a selected group of leaflets suitable for combining together in a prosthetic heart valve.

In an exemplary embodiment, the individual leaflets 28 are deflection tested and leaflets are selected which produced a total deflection of between 0.170 and 0.340" for valve sizes of 25 to 31 mm. Furthermore, for reliability, it is preferred that only leaflets be used for which the fourth and fifth readouts differ within a predetermined range, for example between plus or minus 0.003 inches.

To evaluate the effect of selecting and combining tissue leaflets in 29 mm CEP valves, four valves were manufactured and tested. Two leaflets were selected to have similar deflection values. The third leaflet deflection value was varied from approximately 0.010" to 0.040" compared to the other leaflets as shown in Table II.

TABLE II

| Valve Number | Deflection of Leaflets 1 & 2 | Deflection of Leaflet 3 | Δ Deflection |
|---|---|---|---|
| 13559 | 0.298 | 0.310 | 0.012 |
| 13560 | 0.254 | 0.277 | 0.023 |
| 13561 | 0.238 | 0.269 | 0.031 |
| 13562 | 0.277 | 0.317 | 0.040 |

The valves listed in Table II were placed into a pulsatile flow simulator, and testing performed per conventional protocol. The differential pressure for the testing was 200 mm Hg per Food and Drug Administration guidelines. The valve commissure deflection for each valve was measured as shown in Table III.

TABLE III

| Valve No. | Cycle No. | Comm. 1 Actual (mm) | Comm. 2 Actual (mm) | Comm. 3 Actual (mm) | Average (mm) | Std. Dev. |
|---|---|---|---|---|---|---|
| 13559 | 1 | 0.89 | 1.10 | 0.78 | 0.92 | 0.16 |
|  | 2 | 0.89 | 1.10 | 0.78 | 0.92 | 0.16 |
|  | 3 | 0.86 | 1.13 | 0.79 | 0.93 | 0.18 |
| 13560 | 1 | 1.05 | 1.39 | 1.21 | 1.22 | 0.17 |
|  | 2 | 1.02 | 1.39 | 1.23 | 1.21 | 0.19 |
|  | 3 | 1.05 | 1.42 | 1.23 | 1.23 | 0.19 |
| 13561 | 1 | 1.26 | 1.32 | 1.07 | 1.22 | 0.13 |
|  | 2 | 1.26 | 1.36 | 1.08 | 1.23 | 0.14 |
|  | 3 | 1.23 | 1.32 | 1.08 | 1.21 | 0.12 |
| 13562 | 1 | 1.07 | 1.32 | 0.84 | 1.08 | 0.24 |
|  | 2 | 1.07 | 1.32 | 0.82 | 1.07 | 0.25 |
|  | 3 | 1.05 | 1.36 | 0.84 | 1.08 | 0.26 |
| Average |  |  |  |  | 1.11 |  |
| Std. Dev. |  |  |  |  |  | 0.16 |

Proper coaptation was observed in valves 13559, 13560, and 13561, where the mismatch between leaflets 1 and 2 and leaflet 3 was less than approximately 0.030". Thus, from tis particular study, leaflets which have deflection values differing by less than approximately 0.030" are suitably grouped for combining in a heart valve. Of course, this test applies to 29 mm CEP valves made from selected bovine pericardium, and there are a variety of parameters which could alter the conclusion regarding acceptable deflection correlation. Furthermore, the conclusion was based on measured valve commissure deflection, which is one predictor of prolonged leaflet coaptation. A desirable selection methodology, therefore, is to obtain a collection of similarly sized leaflets, apply a load to each leaflet, observe the resulting strain response, and sort the leaflets based on their respective strain responses. Additionally, the leaflets are preferably chemically fixed prior to testing and a droop test is used in conjunction with the deflection test results.

The present invention additionally teaches a multi-leaflet bioprosthetic heart valve with leaflets selected to have observed deflection responses within a certain range. The average deflection in the range depends on a number of variables, as explained above, and the breadth of the range may depend on empirical test results of assembled valves, such as the commissure deflection data included in Table III. In one exemplary embodiment, however, a 29 mm multi-leaflet bioprosthetic CEP heart valve comprising glutaraldehyde-fixed bovine pericardium tissue leaflets includes at least two leaflets having a deflection of within 0.030 inches as measured using the exemplary testing method and apparatus, with a mass sufficient to create stresses in the leaflets of between 300 and 600 kPa.

It should be noted that the present invention is best suited for categorizing and selecting leaflets having varying material properties from leaflet to leaflet, such as in bovine pericardium. Recent advances in bioprosthetic materials enable manufacturers to produce leaflets by growing tissue on a matrix. Such material may also exhibit nonuniformities in individual leaflets and could be grouped and/or selected in accordance with the present invention. Another type of tissue for which the present invention may prove valuable in selecting leaflets is a composite or laminate substrate on which a cell growth covering is formed. Alternatively, the present selection methods and apparatuses may be applicable to leaflets made from materials with more uniform properties, such as synthetically fabricated or extruded collagen sheets. Though the bulk material properties of these latter materials may be more predictable, individual testing of leaflets is believed desirable to more accurately assess the subsequent dynamic response of the leaflets in use. In addition, testing of leaflets using a setup which closely simulates the particular heart valve in which the leaflet will be used is desirable, in addition to the pre-existing knowledge of the material properties. For these more uniform leaflets, testing of a sample of leaflets from a specific manufactured batch may suffice.

In closing it is to be understood that the embodiments of the invention disclosed herein are illustrative of the principles of the invention and that other modifications may be employed which are within the scope thereof. Accordingly, the present invention is not limited to that precisely as shown and described in the specification.

What is claimed is:

1. A method of selecting leaflets for an implantable heart valve, comprising the steps of:
    providing a collection of similarly sized leaflets;
    applying a load to each leaflet;
    observing the strain response in each leaflet from applying the load; and
    sorting the leaflets based on their respective strain responses.

2. The method of claim 1, wherein the step of providing a collection includes providing a collection of natural tissue leaflets.

3. The method of claim 2, further including the step of chemically fixing the leaflets prior to testing.

4. The method of claim 2, wherein the step of providing a collection of natural tissue leaflets includes providing a collection of bovine pericardium leaflets.

5. The method of claim 1, wherein the step of providing a collection of leaflets includes providing a collection of leaflets having a matrix and natural tissue ingrowth.

6. The method of claim 1, wherein the step of providing a collection of leaflets includes providing a collection of leaflets having a substrate on which is formed a cell growth covering.

7. The method of claim 1, wherein the step of providing a collection of leaflets includes providing a collection of extruded collagen leaflets.

8. The method of claim 1, wherein the step of applying a load comprises applying a load sufficient to create an average stress in at least some of the leaflets within a generally linear, high modulus region of a stress/strain curve of the leaflet material.

9. The method of claim 1, further including the step of applying a load for a predetermined number of times prior to observing the strain response.

10. The method of claim 9, wherein the predetermined number is at least three.

11. The method of claim 1, further including the steps of:
performing an intrinsic load test on the leaflets; and
sorting the leaflets based on the intrinsic load test results.

12. The method of claim 1, wherein the step of sorting the leaflets comprises forming subgroups of leaflets having a strain response within a predetermined range.

13. The method of claim 12, wherein the step of forming subgroups of leaflets having a strain response within a predetermined range comprises a measuring a deflection of each leaflet resulting from applying a load thereto, and forming a subgroup of leaflets each having a deflection within about 0.030 inches of the others.

14. A method of testing a leaflet for use in an implantable heart valve, comprising the steps of:
mounting the leaflet in a framing assembly so that portions which are to be sutured in the valve are held stationary, wherein the leaflet defines a cusp edge and a coapted edge generally opposite the cusp edge, and the framing assembly includes an upper member and a lower member, the lower member having a recess for receiving at least the cusp edge of the leaflet, the upper member being shaped to mate over the recess, and the framing assembly defining a cavity circumscribed by the recess, the step of mounting including positioning the leaflet in the recess and piercing the leaflet cusp edge with needles extending between and supported from movement by the upper and lower members, to hold at least the cusp edge of the leaflet stationary;
applying a load to the leaflet in a location adapted to simulate a point at which an average load is applied in the valve; and
sensing the resulting strain in the leaflet.

15. The method of claim 14, wherein the leaflet is made of natural tissue and further including the step of chemically fixing the leaflet prior to testing.

16. The method of claim 14, wherein the step of applying a load comprises applying a mechanical deflector to an upper surface of the leaflet over the cavity.

17. The method of claim 14, further including the step of recording the sensed strain.

18. The method of claim 17, further including applying a load at least twice before recording the sensed strain.

19. The method of claim 14, further including testing a second leaflet and correlating the results of the applied load tests for the two leaflets.

20. The method of claim 14, further including the step of performing a droop test on the leaflet by extending the leaflet over the end of a structure, and observing the resulting droop of the extended end of the leaflet.

21. The method of claim 20, further including testing a second leaflet and correlating the results of the droop tests and applied load tests for the two leaflets.

22. The method of claim 14, wherein the leaflet is made of a leaflet material, and the step of applying a load comprises applying a load sufficient to stress the leaflet within a generally linear high modulus region of a stress/strain curve of the leaflet material.

23. The method of claim 14, wherein the step of applying a load comprises applying a load sufficient to stress the leaflet between 300 and 600 kPa.

24. The method of claim 14, wherein the location at which the load is applied comprises an idealized concentrated load point and the step of applying a load comprises applying a load to a distributed area of the leaflet.

25. The method of claim 14, wherein the leaflet is made of a matrix and natural tissue ingrowth.

26. The method of claim 14, wherein the leaflet is made of a substrate on which is formed a cell growth covering.

27. The method of claim 14, wherein the leaflet is made of extruded collagen.

28. A method of testing a leaflet for use in an implantable heart valve, wherein the leaflet defines a cusp edge and a coapting edge generally opposite the cusp edge, comprising the steps of:
positioning the leaflet in a frame assembly including an upper member and a lower member, the lower member having a recess for receiving and securing the cusp edge of the leaflet the user member being shaped to mate over the recess, and the framing assembly further defining a cavity circumscribed by the recess;
supporting the leaflet by piercing the leaflet cusp edge with needles extending between and supported from movement by the upper and lower members to hold at least the cusp edge of the leaflet stationary such that a mid-portion remains unsupported;
applying a load to the mid-portion of the leaflet; and
sensing the resulting strain at the mid-portion of the leaflet.

29. The method of claim 28, wherein the leaflet is made of natural tissue and further including the step of chemically fixing the leaflet prior to testing.

30. The method of claim 28, wherein the stop of applying a load comprises applying a mechanical deflector to the mid-point of the leaflet over the cavity.

31. The method of claim 28, further including the step of recording the sensed strain.

32. The method of claim 31, further including applying the load at least twice to the leaflet before recording the sensed strain.

33. The method of claim 28, further including testing a second leaflet and correlating the results of the applied load tests for the two leaflets.

34. The method of claim 28, further including the step of performing a droop test on the leaflet by extending the leaflet over the end of a structure, and observing the resulting droop of the extended end of the leaflet.

35. The method of claim 34, further including testing a second leaflet and correlating the results of the droop tests and applied load tests for the two leaflets.

36. The method of claim 28, wherein the leaflet is made of a leaflet material, and the step of applying a load comprises applying a load sufficient to stress the leaflet within a generally linear high modulus region of a stress/strain curve of the leaflet material.

37. The method of claim 28, wherein the step of applying a load comprises applying a load sufficient to stress the leaflet between 300 and 600 kPa.

38. The method of claim 28, wherein the location at which the load is applied comprises an idealized concentrated load point and the step of applying a load comprises applying a load to EL distributed area of the leaflet.

39. The method of claim 28, wherein the leaflet is made of a matrix and natural tissue ingrowth.

40. The method of claim 28, wherein the leaflet is made of a substrate on which is formed a cell growth coveting.

41. The method of claim 28, wherein the leaflet is made of extruded collagen.

* * * * *